United States Patent [19]

Grozinger et al.

[11] Patent Number: 5,668,287

[45] Date of Patent: Sep. 16, 1997

[54] METHOD FOR THE PREPARATION OF 3-AMINO-2-CHLORO-4-METHYLPYRIDINES

[75] Inventors: Karl G. Grozinger, Ridgefield; Karl D. Hargrave, Brookfield; Julian Adams, Ridgefield, all of Conn.

[73] Assignee: Boehringer Ingelheim Pharmaceuticals, Inc., Ridgefield, Conn.

[21] Appl. No.: 514,648

[22] Filed: Aug. 14, 1995

Related U.S. Application Data

[63] Continuation of Ser. No. 308,042, Sep. 16, 1994, abandoned, which is a continuation of Ser. No. 187,574, Jan. 26, 1994, abandoned, which is a continuation of Ser. No. 714,549, Jun. 11, 1991, abandoned.

[51] Int. Cl.[6] .................................................. C07D 213/02
[52] U.S. Cl. .................................... 546/250; 546/311
[58] Field of Search ............................ 546/250, 311

[56] References Cited

U.S. PATENT DOCUMENTS

| 2,372,690 | 4/1945 | Stiller | 546/250 |
|---|---|---|---|
| 3,703,582 | 11/1972 | Shen et al. | 546/311 |
| 4,395,554 | 7/1983 | Chang | 546/250 |

OTHER PUBLICATIONS

Lucas, Organic Chemistry, 2nd Edition, 1953, pp. 374–375.
Morrison et al, Organic Chemistry, 2nd Ed, 1966, pp. 728 & 535–738.

Bobbitt et al. J. of Organic Chemistry, vol. 25, 1960, pp. 560–564.

Shickh et al. Berichte der Deutschen Chem, Gesell. 1936, pp. 2593–2605.

Morisawa et al, J. of med. Chem, vol. 21, No. 2, 1978, pp. 194–199.

Lounasmaa et al. Tetrahedron, vol. 33, 1977, pp. 113–117.

Schmitz et al. Archiv de Pharmazie, vol. 308, 1975, pp. 433–437.

*Primary Examiner*—Zinna Northington Davis
*Attorney, Agent, or Firm*—R. P. Raymond; Alan R. Stempel

[57] ABSTRACT

A process for the preparation of a 3-amino-2-chloro-4-alkylpyridine of the formula:

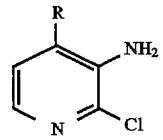

wherein R is alkyl of from one to three carbon atoms, an intermediate in the preparation of certain 5,11-dihydro-6H-dipyrido[3,2-b:2',3'-e][1,4]diazepine compounds useful in the prevention and treatment of HIV infection.

5 Claims, No Drawings

METHOD FOR THE PREPARATION OF 3-AMINO-2-CHLORO-4-METHYLPYRIDINES

This is a continuation of application Ser. No. 308,042, filed Sep. 16, 1994, now abandoned, which is a continuation of application Ser. No. 187,574, filed Jan. 26, 1994, now abandoned, which is a continuation of application Ser. No.714,549, filed Jun. 11, 1991, now abandoned.

FIELD OF THE INVENTION

This invention relates to a novel method for preparing certain 3-amino-2-chloro-4-alkylpyridines.

BACKGROUND OF THE INVENTION

U.S. Pat. No. 5,366,972, filed Oct. 19, 1990, entitled "5,11-Dihydro-6H-Dipyrido[3,2-b:2',3'-e][1,4]Diazepines and Their Use in the Prevention or Treatment of HIV Infection", describes novel 5,11-dihydro-6H-dipyrido[3,2-b:2',3'-e][1,4]diazepines useful in the prevention and treatment of HIV infection and methods for preparing these compounds.

3-Amino-2-chloro-4-alkylpyridines are useful intermediates in the preparation of 4-alkyl-5,11-dihydro-6H-dipyrido[3,2-b:2',3'-e]-[1,4]diazepines.

SUMMARY OF THE INVENTION

3-Amino-2-chloro-4-alkylpyridines prepared by the novel process of this invention have the formula:

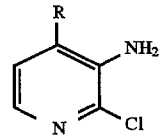
(I)

wherein R is alkyl of from one to three carbon atoms.

The process for this invention for the preparation of the compound of formula I is outlined below:

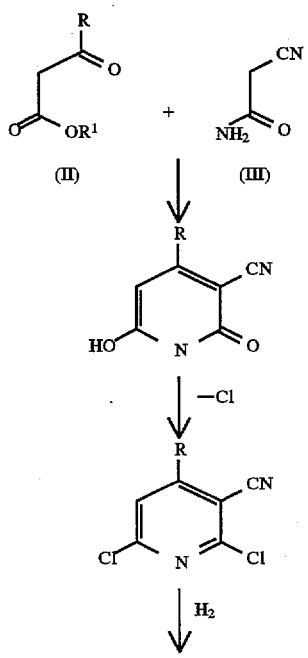

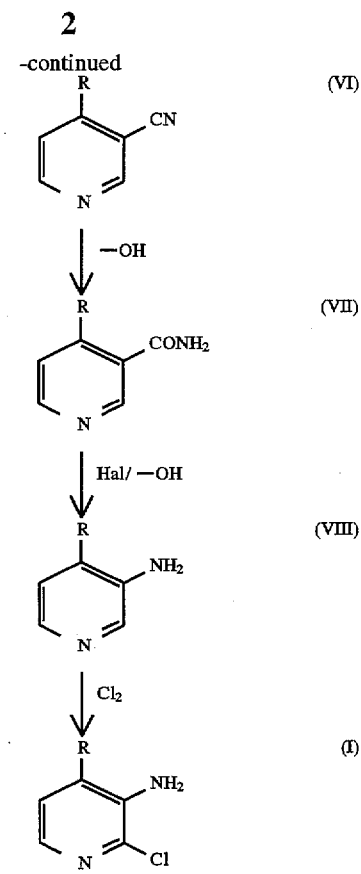

DETAILED DESCRIPTION OF THE INVENTION

The novel process of this invention for preparing the 3-amino-2-chloro-4-alkylpyridine of formula I comprises the following steps:

Step 1, reacting a compound having the formula:

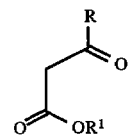
(II)

wherein R and $R^1$ are each alkyl of from one to three carbon atoms, with cyanoacetamide

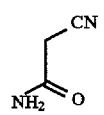
(III)

in the presence of an organic solvent such as methanol or ethanol, with a base, such as KOH, at a temperature ranging from 50° C. to 80° C., for 4 to 8 hours, to produce a compound of the formula:

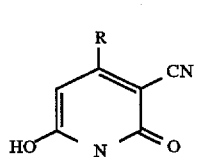
(IV)

Step 2, reacting the compound produced in Step 1 with a chlorinating agent, such as phenylphosphonic dichloride or inorganic acid halides such as phosphorous oxychloride, at a temperature of 110° C. to 180° C., for 6 to 24 hours, to produce a compound of the formula:

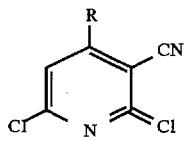

Step 3, hydrogenating the compound produced in Step 2 in the presence of an organic solvent such as methanol or tetrahydrofuran (THF), with a hydrogenation catalyst such as palladium chloride or a palladium metal, at 50 to 150 psi, at a temperature of 20° C. to 100° C., for 6 to 24 hours, to produce a compound of the formula:

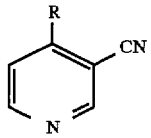

Step 4, mixing the compound produced in Step 3 with an ion exchange resin such as Amberlite IRA-400-OH, or with one equivalent of a base or an acid, at a temperature of 60° C. to 100° C. for 1 to 4 hours, to produce a compound of the formula:

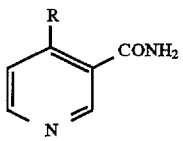

Step 5, reacting the compound produced in Step 4 with a base such as NaOH and a halide such as bromine or chlorine, for 1 to 4 hours, at 0° C. to 85° C., to produce a compound of the formula:

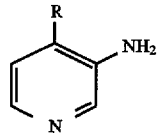

Step 6, contacting the compound produced in Step 5 with chlorine gas at a pH or 0.01 to 2, at a temperature of 5° C. to 30° C., for 0.5 to 2 hours, to produce the compound of formula I.

Example I illustrates the preparation of the 3-amino-2-chloro-4-alkylpyridines of formula I.

EXAMPLE I

Preparation of 3-Amino-2-Chloro-4-Methylpyridine

A) Preparation of 3-Cyano-2,6-Dihydro-4-Methylpyridine

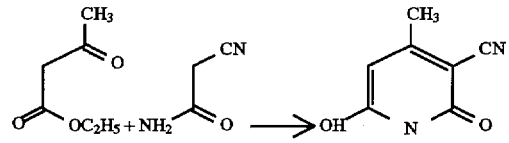

A mixture of 336 g (4 moles) of cyanoacetamide, 507 ml (520 g, 4 moles) of ethyl acetoacetate, and 850 ml of methanol was warmed to attain solution then 275 g (4.18 moles) of potassium hydroxide dissolved in 200 ml of methanol was added during 2 hours with stirring. During the addition a white precipitate formed and more methanol was added to prevent caking. The mixture was heated to reflux, stirred for 8 hours, cooled and filtered. The white precipitate was washed with methanol. The mono potassium salt was dissolved in warm water, filtered, cooled, acidified with concentrated hydrochloric acid, filtered, washed with water, and dried at 90° C. to yield 535 g (89%).

B) Preparation of 3-Cyano-2,6-Dichloro-4-Methylpyridine

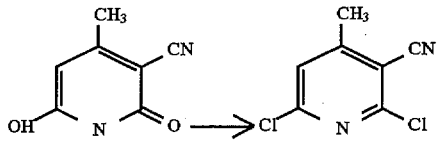

Method 1

3-Cyano-2,6-dihydroxy-4-methylpyridine (30 g, 0.2 mole) and phosphorous oxychloride (80 ml) were placed in a glass lined stainless steel autoclave and heated to 110°–140° C. for 18 hours. (A pressure of 110–130 psi was obtained.) After cooling, the mixture was poured into 300 ml of warm water (30°–40° C.). During the hydrolysis, the mixture was maintained at 30°–40° C. by the intermittent addition of ice. The crystalline product was filtered and washed with water and dried. The material was crystallized from hot ethanol to yield 33.7 g (mp 102°–106° C.) (90%).

Method 2

A 5 liter 3-neck round bottom flask equipped with overhead stirrer, thermometer, and reflux condenser was charged with 810 ml (5.7 mole) phenylphosphonic dichloride. The solution was heated with stirring to an internal temperature of 100° C., then 288 g (1.9 mole) of 2,6-dihydroxy-3-cyano-4-methylpyridine was added in portions over 45 minutes, keeping the internal temperature at 100°–105° C. The mixture was then heated to 140°–145° C. for 2 hours. After cooling the solution to 70° C., 2 liters of toluene was added with stirring. The mixture was poured cautiously over 2 liters of H$_2$O, and stirred for one hour at room temperature. The organic layers were separated. The aqueous phase was back-extracted with 2 liter of toluene. During the extraction, C$_6$H$_5$PO$_2$ separated, which was filtered off. The solid was washed with toluene and finally discarded (wt. 478 g). The combined organic layers were dried over anhydrous Na$_2$SO$_4$, filtered, and the solvent evaporated. The solid was stirred with ethanol, and air dried to give a light yellow solid, wt: 272.5 g (76.7%); mp 100°–105°C.

C) Preparation of 3-Cyano-4-Methylpyridine

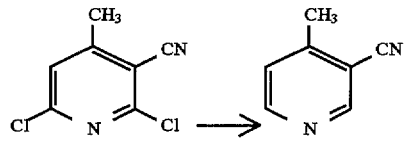

Method 1

A mixture of 40.0 g (0.214 mole) of 2,4-dichloro-3-cyano-4-methylpyridine, 35.0 g of anhydrous sodium acetate, 1.0 g of palladium (II) chloride, and 200 ml of methanol was hydrogenated in a stirred PARR hydrogenator at 50 psi and 60° C. for 24 hours. The catalyst was filtered through Celite and washed with methanol. The filtrate was concentrated to a light orange oil to which 100 ml of water was added. The mixture was neutralized with solid sodium bicarbonate. The product was extracted with 2×200 ml of ether. The combined organics were dried over anhydrous sodium sulfate and concentrated to a dark yellow oil, which crystallized on cooling to give 17.6 g (69.7%) of yellow needles.

Method 2

The same procedure as described in Method 1 was used except that 3.2 g of 10% Pd/C was substituted for the palladium (II) chloride. 20.0 g (79.0%) of yellow needles were produced.

D) Preparation of 4-Methyl-3-Pyridinecarboxamide

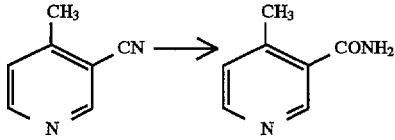

To a stirred mixture of 11.7 g (0.099 mole) of 3-cyano-4-methylpyridine in 50 ml of water was added 14.7 g of pre-washed ion exchange resin (Amberlite IRA-400-OH). The mixture was heated to reflux for three hours, then cooled to 60° C. The ion exchange resin was filtered and washed with water. The filtrate was concentrated under vacuum to a yellow solid. The mixture was stirred with high boiling petroleum ether, filtered, and dried under vacuum at 80° C. to yield 8.8 g (65%) of the amide.

E) Preparation of 3-Amino-4-Methylpyridine

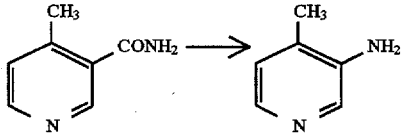

To a solution of 7.8 g (0.196 mole) of sodium hydroxide in 75 ml of water was added 3.0 ml (0.587 mole) of bromine at 0° –5° C. To the cold sodium hypobromite solution so produced was added 7.0 g (0.0514 mole) of 4-methyl-3-pyridine carboxamide at once. The ice bath was removed and the reaction mixture was allowed to warm to room temperature. The resulting yellow solution was warmed to 70°–75° C. for one hour, then cooled to room temperature. The product was extracted with 3×100 ml of ethyl acetate. The combined extracts were dried over anhydrous sodium sulfate, filtered, and concentrated to a solid. The product was stirred with petroleum ether and filtered, dried at 50° C. to yield 4.2 g (75.5%) mp 99°–101° C.

F) Preparation of 3-Amino-2-Chloro-4-Methylpyridine

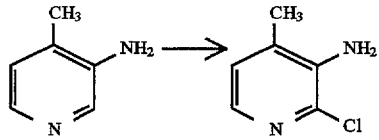

3-Amino-4-methylpyridine (21.6 g, 0.2 mole) was suspended in 75 ml of water at room temperature. The mixture was dissolved by the addition of 25 ml conc. hydrochloric acid. The solution was cooled to 20° C. and 15.6 g (0.22 mole) of chlorine gas was introduced through an inlet tube reaching below the surface of the reaction mixture over 25 minutes. The mixture was stirred under a nitrogen purge for an additional 30 minutes, then cooled to 10° C. and basified by the addition of 70 mL of a 12.5 N. sodium hydroxide solution. Additional water (100 mL) was added to maintain efficient agitation of the mixture. The precipitate was collected, washed with water and dried to give 14.5 g of the title product. The aqueous phase was extracted with 3 times 100 mL of methylene chloride. The organic phases were washed with water, dried over magnesium sulfate, and concentrated to give an additional 9.4 g, mp 62–64° C. Total yield, 23.9 g (84%).

What is claimed is:

1. A process for the preparation of 3-amino-2-chloro-4-methylpyridine, which comprises the steps of:

a) reacting ethyl acetoacetate with cyanoacetamide and a base, in the presence of an organic solvent, at a temperature of from 60° C. to 80° C., for 1 to 4 hours, to produce 3-cyano-2,6-dihydro-4-methylpyridine;

b) reacting the 3-cyano-2,6-dihydro-4-methylpyridine produced in a) with a chlorinating agent which is selected from the group consisting of phenylphosphonic dichloride and phosphorous oxychloride, at a temperature of 110° C. to 180° C., for 6 to 24 hours, to produce 3-cyano-2,6-dichloro-4-methylpyridine;

c) hydrogenating the 3-cyano-2,6-dichloro-4-methylpyridine produced in b) in the presence of an organic solvent, with an hydrogenation catalyst selected from the group consisting of palladium (II) chloride and 10% Pd/C, at 50 to 150 psi, at a temperature of from 20° C. to 100° C., for 6 to 24 hours, to produce 3-cyano-4-methylpyridine;

d) hydrolyzing the 3-cyano-4-methylpyridine produced in c), with a strongly anionic ion exchange resin or one equivalent of a base or an acid, at a temperature of 60° C. to 100° C., for 1 to 4 hours, to produce 4-methyl-3-pyridinecarboxamide;

e) reacting the 4-methyl-3-pyridinecarboxamide produced in d) with a strong base and a halide selected from bromine and chlorine (to produce the hypobromite or hypochlorite), at a temperature of from 0° C. to 85° C., for 1 to 4 hours, to produce 3-amino4-methylpyridine;

f) contacting the 3-amino-4-methylpyridine produced in e) with chlorine gas, at a pH of 0.01 to 2, at a temperature of 5° C. to 30° C. for 0.5 to 2 hours, to produce 3-amino-2-chloro-4-methylpyridine.

2. The process as recited in claim 1 wherein, in step (a), the base is KOH.

3. The process as recited in claim 1 wherein, in step b), the compound produced in a) is reacted with phosphorous oxychloride and then any excess phosphorous oxychloride is hydrolyzed at a temperature of from 30° C. to 50° C. for 0.5 to 1 hour.

4. The process as recited in claim 1, wherein, in step d), the 3-cyano-4-methylpyridine produced in c), is hydrolyzed with a strongly anionic ion exchange resin.

5. The process as recited in claim 1 wherein, in step (e) the base is NaOH.

* * * * *